(12) United States Patent
El Haddad

(10) Patent No.: US 10,335,052 B2
(45) Date of Patent: Jul. 2, 2019

(54) DETECTION OF PULMONARY VEIN ISOLATION

(71) Applicant: UNIVERSITEIT GENT, Ghent (BE)

(72) Inventor: Milad El Haddad, Ghent (BE)

(73) Assignee: UNIVERSITEIT GENT, Ghent (BE)

( * ) Notice: Subject to any disclaimer, the term of this patent is extended or adjusted under 35 U.S.C. 154(b) by 289 days.

(21) Appl. No.: 15/309,543

(22) PCT Filed: May 4, 2015

(86) PCT No.: PCT/EP2015/059664
§ 371 (c)(1),
(2) Date: Nov. 8, 2016

(87) PCT Pub. No.: WO2015/169724
PCT Pub. Date: Nov. 12, 2015

(65) Prior Publication Data
US 2017/0181655 A1    Jun. 29, 2017

Related U.S. Application Data

(60) Provisional application No. 61/990,803, filed on May 9, 2014.

(51) Int. Cl.
*A61B 5/00*     (2006.01)
*A61B 5/0452*   (2006.01)
*A61B 5/0456*   (2006.01)
*A61B 5/046*    (2006.01)

(52) U.S. Cl.
CPC .......... *A61B 5/04525* (2013.01); *A61B 5/046* (2013.01); *A61B 5/0456* (2013.01); *A61B 5/7221* (2013.01); *A61B 5/7282* (2013.01)

(58) Field of Classification Search
CPC ... A61B 5/04526; A61B 5/0456; A61B 5/064; A61B 5/721; A61B 5/7282
See application file for complete search history.

(56) References Cited

U.S. PATENT DOCUMENTS

| 2007/0038056 A1 | 2/2007 | Pappone et al. |
| 2010/0023081 A1 | 1/2010 | Audet et al. |
| 2012/0089032 A1 | 4/2012 | Park et al. |

FOREIGN PATENT DOCUMENTS

| CN | 202335863 U  | 7/2012 |
| EP | 2540245 A1   | 1/2013 |

OTHER PUBLICATIONS

International Search Report for corresponding International PCT Application No. PCT/EP2015/059664, dated Jul. 7, 2015.

*Primary Examiner* — Paula J Stice
(74) *Attorney, Agent, or Firm* — Workman Nydegger

(57) ABSTRACT

A device for analyzing electrophysiological data is disclosed. The device generates a signal indicative for a presence of a pulmonary vein potential component using processing means adapted for performing a stepwise analysis of the electrophysiological data. A corresponding method and computer application for installing on a device are also described.

20 Claims, 9 Drawing Sheets

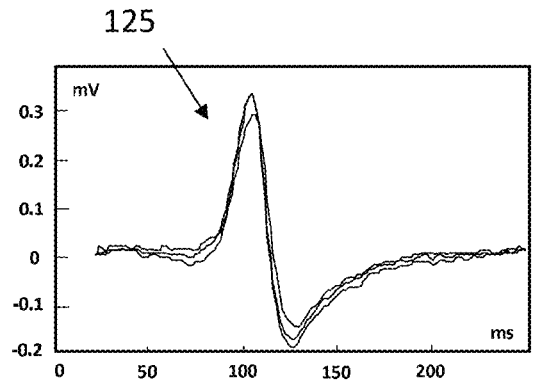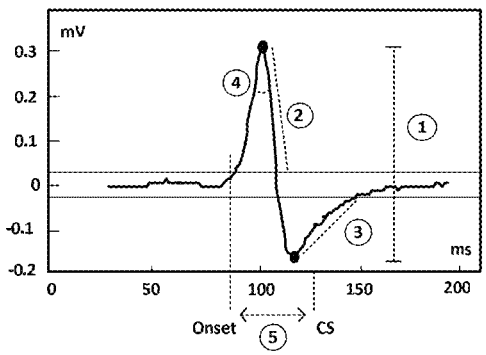
FIG. 5   FIG. 6
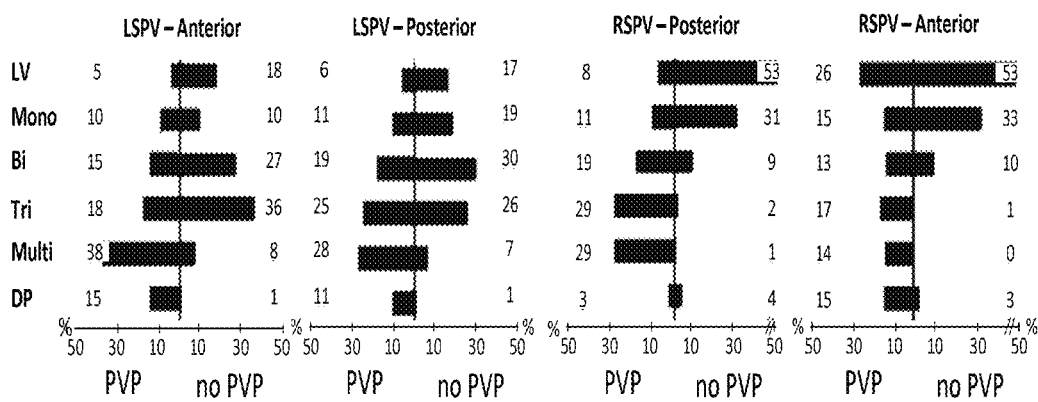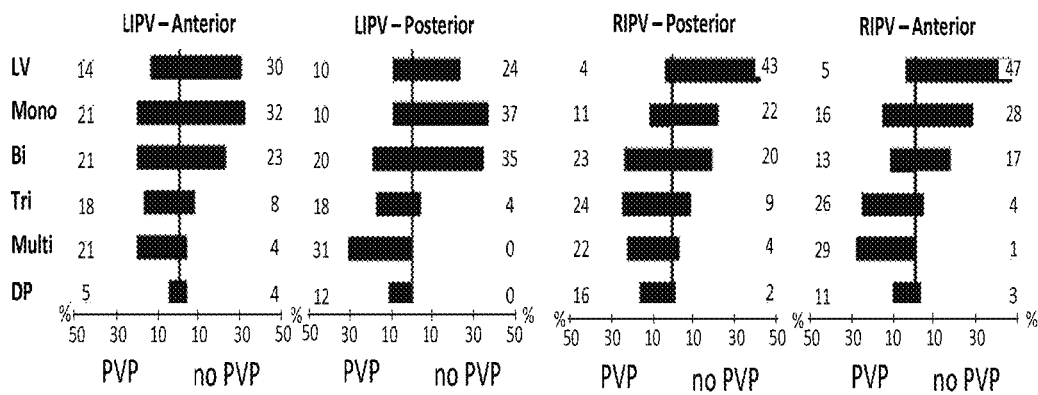
FIG. 7

| PV recording at the LA-PV junction (RSPV, before PVI) | Hemisphere | Averaged potentials | Morphology | Prevalence PVP, no PVP | Likelihood that PV has PVP (Step 1) |
|---|---|---|---|---|---|
| RSPV 1-2 | Ant | | Triphasic | 17, 1 | |
| RSPV 2-3 | Post | | Multiphasic | 29, 1 | |
| RSPV 3-4 | Post | | Multiphasic | 29, 1 | $\frac{197-28}{197+28}$ |
| RSPV 4-5 | Post | | Multiphasic | 29, 1 | |
| RSPV 5-6 | Post | | Multiphasic | 29, 1 | = 0.75 |
| RSPV 6-7 | Post | | Biphasic | 19, 9 | (>0.33) |
| RSPV 7-8 | Ant | | Biphasic | 13, 10 | => PVP |
| RSPV 8-9 | Ant | | Double potentials | 15, 3 | |
| RSPV 9-10 | Ant | | Triphasic | 17, 1 | |
| | | | | 197, 28 | |

FIG. 8

| PV recording at the LA-PV junction (LSPV, before PVI) | Hemisphere | Averaged potentials | Morphology | prevalence PVP, no PVP | Number of specific parameters PVP, no PVP | Type prevalence x num. of parameters PVP, no PVP |
|---|---|---|---|---|---|---|
| LSPV 1-2 | Ant | ** | Multiphasic 38, 8 | | 2, 0 | 76, 0 |
| LSPV 2-3 | Ant | | Biphasic 15, 27 | Likelihood that PV has PVP (Step 1) | 0, 0 | Likelihood that PV has PVP (Step 2) 0, 0 |
| LSPV 3-4 | Post | | Triphasic 25, 26 | | 0, 0 | 0, 0 |
| LSPV 4-5 | Post | * | Triphasic 25, 26 | $\frac{220-228}{220+228}$ | 1, 0 | $\frac{176-0}{176+0}$ 25, 0 |
| LSPV 5-6 | Post | *** | Triphasic 25, 26 | = -0.04 | 3, 0 | 75, 0 = 1 |
| LSPV 6-7 | Ant | | Triphasic 18, 36 | (-0.04_0.12) | 0, 0 | 0, 0 (>0) |
| LSPV 7-8 | Ant | | Triphasic 18, 36 | => | 0, 0 | 0, 0 |
| LSPV 8-9 | Ant | | Triphasic 18, 36 | continue to step 2 | 0, 0 | 0, 0 => PVP |
| LSPV 9-10 | Post | | Multiphasic 28, 7 | | 0, 0 | 0, 0 |
| | | | | 220, 228 | | 176, 0 |

FIG. 9

PV recording at the LA-PV junction (P10, LIPV, after PVI)

| | | | | | | |
|---|---|---|---|---|---|---|
| LIPV 1-2 | ~~~ | Post | ~~~ | Monophasic | 10 | 37 |
| LIPV 2-3 | ~~~ | Post | ~~~ | Monophasic | 10 | 37 |
| LIPV 3-4 | ~~~ | Ant | ~~~ | Monophasic | 21 | 32 |
| LIPV 4-5 | ~~~ | Ant | ~~~ | Monophasic | 21 | 32 |
| LIPV 5-6 | ~~~ | Ant | ~~~ | Monophasic | 21 | 32 |
| LIPV 6-7 | ~~~ | Ant | ~~~ | Biphasic | 21 | 25 |
| LIPV 7-8 | ~~~ | Post | ~~~ | Biphasic | 20 | 35 |
| LIPV 8-9 | ~~~ | Post | ~~~ | Monophasic | 10 | 37 |
| LIPV 9-10 | ~~~ | Post | ~~~ | Monophasic | 10 | 37 |
| | | | | | 144 | 302 |

$$\frac{144 - 302}{144 + 302} \times 100\% = -35\%$$

DETECTION OF PULMONARY VEIN ISOLATION

FIELD OF THE INVENTION

The invention relates to the field of electrophysiological data analysis. More specifically it relates to a method and device for detection, e.g. an automatic algorithmic detection or verification carried out by a computing device, of electrical isolation between a pulmonary vein and the left atrium of the heart.

BACKGROUND OF THE INVENTION

Atrial fibrillation is a common form of cardiac arrhythmia. Although not all details on the mechanism of atrial fibrillation are clear at present, it has been observed that atrial fibrillation is often triggered from the pulmonary veins (PV). Atrial fibrillation may be treated by electrically isolating the pulmonary veins from the heart, e.g. from the left atrium, for example by applying catheter-based radiofrequency ablation around the pulmonary veins. Such therapeutic strategy may be particularly useful for patients with drug-resistant and symptomatic recurrent atrial fibrillation. For the ablation therapy to be successful, a good electrical isolation, e.g. substantially complete or complete electrical isolation, of the pulmonary veins is required.

It is known in the art that such electrical isolation can be verified by examining electrogram data recorded at the junction between the pulmonary vein and the left atrium during the ablation procedure, for example bipolar electrograms obtained at the junction by a circular mapping catheter, e.g. LASSO electrocardiogram data. The electrogram data contain far field potentials (FFP) generated by other anatomical structures in the heart, such as the atria, the left atrium appendage, the mitral annulus and the ventricles. When the electrical isolation between the pulmonary vein and the left atrium is insufficient, the electrograms contain both pulmonary vein potentials and far field potentials. On the other hand, when the pulmonary vein is isolated from the left atrium, the atrial electric signals cannot propagate into the pulmonary vein, such that the electrograms only contain far field potentials.

However, interpretation of such electrograms can be a challenging and time-consuming task, even to experienced electrophysiologists. Evaluation of the electrical isolation by visual assessment of the left atrium-pulmonary vein junction (LA-PV) electrogram data may also be assisted by pacing, for example by actively applying an electrical signal and checking whether this signal propagates across an isolation region, e.g. an ablation scar line provided for electrically isolating the pulmonary vein.

Other methods are known in the art for evaluating the electrical isolation indirectly, for example by imaging the lesion formed by the ablation process, e.g. using magnetic resonance imaging or ultrasound imaging. Although such methods may allow a more efficient evaluation, the indirect inference of the electrical insulation condition by such methods may lead to larger lesions being created than necessary in order to account for an uncertainty in verifying a sufficient isolation, or may lead to ineffective treatment when a lesion only appears to be sufficient for electrically isolating the vein.

The present invention relates to the detection of this electrical isolation by automated analysis of electrogram data recorded at the junction between the left atrium of the heart and a pulmonary vein, e.g. recorded during a radio-frequency ablation procedure. Thus, a distinction is made in accordance with a decision algorithm between the case where the electrogram data comprises both pulmonary vein potentials and far field potentials, e.g. where the pulmonary vein is not electrically isolated, and the case where the electrogram data contains only far field potentials, e.g. where the pulmonary vein is electrically isolated.

SUMMARY OF THE INVENTION

It is an object of embodiments of the present invention to provide good means and methods for automated analysis of electrical isolation of the pulmonary vein, e.g. from electrical signals propagating from cardiac structures.

It is an advantage of embodiments of the present invention that interpretation of electrograms can be assisted by an automatic evaluation of electrical isolation. It is a further advantage that such interpretation can be simplified and can be performed in a time-efficient manner.

It is an advantage of embodiments of the present invention that electrical isolation of a pulmonary vein can be efficiently determined without applying an exogenous electrical signal, e.g. a test potential.

It is an advantage of embodiments of the present invention that electrical isolation of a pulmonary vein can be directly inferred from measurements related to electrical signal conduction. The above objective is accomplished by a method and device according to the present invention.

In a first aspect, the present invention relates to a device for analysing electrophysiological data. The device comprises an input means for inputting, e.g. for receiving, at least one electrocardiogram recorded in a junction region between a pulmonary vein and a left atrium of the heart in a subject. The device also comprises a processing means adapted for determining a morphology classification representative of a waveform shape for the or each at least one electrocardiogram. The processing means is furthermore adapted for determining a first value representative of a likelihood that the at least one electrocardiogram comprises a pulmonary vein potential component, in which the determining of the first value takes the morphology classification into account. The device also comprises an output means for generating a signal indicative for the detected presence of the pulmonary vein potential component when the first value satisfies a first predetermined condition and a signal indicative for the detected absence of the pulmonary vein potential component when the first value satisfies a second predetermined condition.

The processing means is furthermore adapted for determining at least one morphological parameter indicative of at least one waveform feature for the or each at least one electrocardiogram. The processing means is also adapted for determining a second value representative of the likelihood that the at least one electrocardiogram comprises the pulmonary vein potential component, in which this determining of the second value takes the at least one morphological parameter and the morphology classification into account. The output means is furthermore adapted for generating a signal indicative for the detected presence of the pulmonary vein potential component when the second value satisfies a third predetermined criterion. A device according to embodiments of the present invention may furthermore comprise a storage means for storing previously recorded prevalence information for the morphological classification. The processing means may be adapted for determining the first value taking this previously recorded prevalence information into account.

In a device according to embodiments of the present invention, the processing means may be furthermore adapted for pre-processing the at least one electrocardiogram by detecting, aligning and/or averaging of a plurality of atrial potentials corresponding to a plurality of heart beats in the or each at least one electrocardiogram.

In a device according to embodiments of the present invention, the input means may be adapted for recording a plurality of electrocardiograms from the pulmonary vein, such that each of the plurality of electrocardiograms is recorded at a plurality of different junction positions between the pulmonary vein and the left atrium of the heart of the subject.

In a device according to embodiments of the present invention, the processing means may be adapted for determining the morphology classification for the or each of the plurality of electrocardiograms.

In a device according to embodiments of the present invention, the processing means may be adapted for determining a number of peaks above a predetermined noise threshold and determining the morphology classification may take into account the determined number of peaks.

In a device according to embodiments of the present invention, the processing means may be adapted for determining an angle between an upstroke and a downstroke of a detected peak and comparing the determined angle with a predetermined angle, wherein the processing means is adapted for determining the morphology classification taking into account said comparing.

In a device according to embodiments of the present invention, the processing means may be adapted for selecting one of a low voltage class, a monophasic peak class, a biphasic peak class, a triphasic peak class and multiphasic peak class when determining the morphology classification.

In a device according to embodiments of the present invention, the processing means may be adapted for determining at least one out of a peak-to-peak amplitude, a maximum slope, a minimal slope, a sharpest peak angle and a time to coronary sinus when determining the at least one morphological parameter.

In a device according to embodiments of the present invention, the processing means may be adapted for determining a hemisphere classification for the or each at least one electrocardiogram.

In a device according to embodiments of the present invention, the input means may be provided for inputting a hemisphere classification for the or each at least one electrocardiogram.

In a device according to embodiments of the present invention, the processing means may be adapted for taking said hemisphere classification into account when determining the first and/or second value.

In a second aspect, the present invention relates to a method for analysing electrophysiological data, e.g. electrocardiogram data. The method comprises obtaining at least one electrocardiogram recorded in a junction region between a pulmonary vein and a left atrium of the heart in a subject, e.g. obtaining at least one such electrocardiogram that is pre-recorded. The method further comprises determining a morphology classification representative of a waveform shape for the or each at least one electrocardiogram. The method also comprises determining a first value representative of a likelihood that the at least one electrocardiogram comprises a pulmonary vein potential component, in which this determining of the first value takes the morphology classification into account. The method further comprises generating a signal indicative for the detected presence of the pulmonary vein potential component when the first value satisfies a first predetermined condition and generating a signal indicative for the detected absence of the pulmonary vein potential component when the first value satisfies a second predetermined condition. The method also comprises determining at least one morphological parameter indicative of at least one waveform feature for the or each at least one electrocardiogram, and determining a second value representative of the likelihood that the at least one electrocardiogram comprises the pulmonary vein potential component, in which this determining of the second value takes the at least one morphological parameter and the morphology classification into account. The method further comprises generating a signal indicative for the detected presence of the pulmonary vein potential component when the second value satisfies a third predetermined criterion.

In a method according to embodiments of the present invention, the steps of determining at least one morphological parameter, determining the second value and generating the signal indicative for the detected presence of the pulmonary vein potential component when the second value satisfies the third predetermined criterion may be performed only when the first value does not satisfy the first criterion and the first value does not satisfy the second criterion.

In a method according to embodiments of the present invention, the determining of the first value may comprise taking previously recorded prevalence information for the morphological classification into account.

A method according to embodiments of the present invention may furthermore comprise pre-processing the at least one electrocardiogram by detecting, aligning and/or averaging of a plurality of atrial potentials corresponding to a plurality of heart beats in the or each at least one electrocardiogram.

In a method according to embodiments of the present invention, obtaining the at least one electrocardiogram may comprise obtaining a plurality of electrocardiograms from the pulmonary vein, each of the plurality of electrocardiograms being recorded at a plurality of different junction positions between the pulmonary vein and the left atrium of the heart of the subject.

In a method according to embodiments of the present invention, the step of determining the morphology classification may be performed for each of the plurality of electrocardiograms.

In a method according to embodiments of the present invention, determining the morphology classification may comprise determining a number of peaks above a predetermined noise threshold.

In a method according to embodiments of the present invention, the step of determining the morphology classification may comprise determining an angle between an upstroke and a downstroke of a detected peak and comparing the determined angle with a predetermined threshold.

In a method according to embodiments of the present invention, determining the morphology classification may comprise selecting one of: a low voltage class, a monophasic peak class, a biphasic peak class, a triphasic peak class, a multiphasic peak class, and a double potentials peak class.

In a method according to embodiments of the present invention, determining the at least one morphological parameter may comprise determining at least one out of: a peak-to-peak amplitude, a maximum slope, a minimal slope, a sharpest peak angle and a time to coronary sinus.

A method according to embodiments of the present invention may further comprise determining a hemisphere classification for the or each at least one electrocardiogram.

In a method according to embodiments of the present invention, determining the first value takes into account the determined hemisphere classification for the or each at least one electrocardiogram.

In a method according to embodiments of the present invention, determining the second value takes into account the determined hemisphere classification for the or each at least one electrocardiogram.

In a third aspect, the present invention relates to a computer program stored on a computer readable medium configured to carry out a method according to embodiments of the second aspect of the present invention.

Particular and preferred aspects of the invention are set out in the accompanying independent and dependent claims. Features from the dependent claims may be combined with features of the independent claims and with features of other dependent claims as appropriate and not merely as explicitly set out in the claims. In particular, one or more of the steps of the method according to the second aspect of the invention could be implemented on the device according to the first aspect of the invention.

These and other aspects of the invention will be apparent from and elucidated with reference to the embodiment(s) described hereinafter.

BRIEF DESCRIPTION OF THE DRAWINGS

FIG. 5 illustrates the alignment and averaging of potentials in a preprocessing step in accordance with embodiments of the present invention.

FIG. 6 illustrates the determining of exemplary morphological parameters in accordance with embodiments of the present invention.

FIG. 7 illustrates an exemplary reference library for determining the first value in accordance with embodiments of the present invention.

FIG. 8 illustrates the determining of the first value in accordance with embodiments of the present invention, applied to data recorded at a right superior pulmonary vein before performing an electrically isolating ablation procedure.

FIG. 9 illustrates the determining of the first and second value in accordance with embodiments of the present invention.

Figure 1:
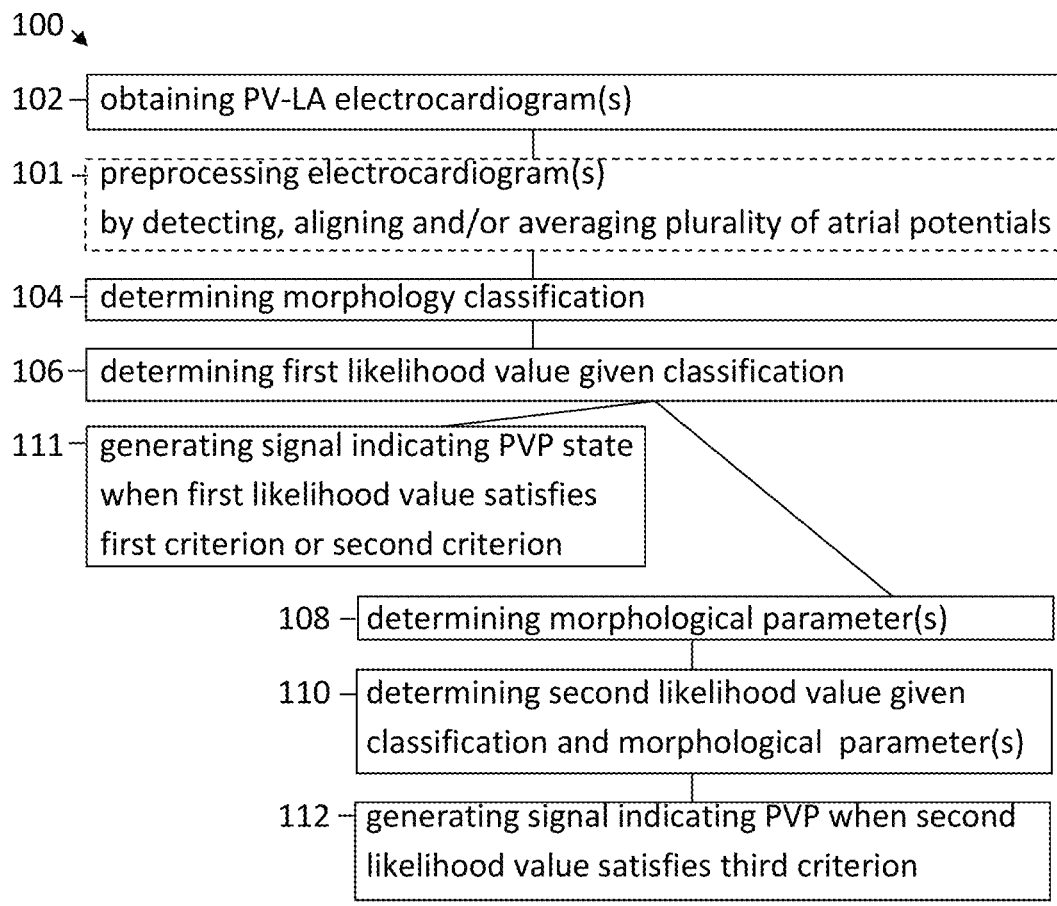
FIG. 1 illustrates a method according to embodiments of the present invention.

The drawings are only schematic and are non-limiting. In the drawings, the size of some of the elements may be exaggerated and not drawn on scale for illustrative purposes.

Any reference signs in the claims shall not be construed as limiting the scope.

In the different drawings, the same reference signs refer to the same or analogous elements.

DETAILED DESCRIPTION OF ILLUSTRATIVE EMBODIMENTS

The present invention will be described with respect to particular embodiments and with reference to certain drawings but the invention is not limited thereto but only by the claims. The drawings described are only schematic and are non-limiting. In the drawings, the size of some of the elements may be exaggerated and not drawn on scale for illustrative purposes. The dimensions and the relative dimensions do not correspond to actual reductions to practice of the invention.

Furthermore, the terms first, second and the like in the description and in the claims, are used for distinguishing between similar elements and not necessarily for describing a sequence, either temporally, spatially, in ranking or in any other manner. It is to be understood that the terms so used are interchangeable under appropriate circumstances and that the embodiments of the invention described herein are capable of operation in other sequences than described or illustrated herein.

Moreover, the terms top, under and the like in the description and the claims are used for descriptive purposes and not necessarily for describing relative positions. It is to be understood that the terms so used are interchangeable under appropriate circumstances and that the embodiments of the invention described herein are capable of operation in other orientations than described or illustrated herein.

It is to be noticed that the term "comprising", used in the claims, should not be interpreted as being restricted to the means listed thereafter; it does not exclude other elements or steps. It is thus to be interpreted as specifying the presence of the stated features, integers, steps or components as referred to, but does not preclude the presence or addition of one or more other features, integers, steps or components, or groups thereof. Thus, the scope of the expression "a device comprising means A and B" should not be limited to devices consisting only of components A and B. It means that with respect to the present invention, the only relevant components of the device are A and B.

Reference throughout this specification to "one embodiment" or "an embodiment" means that a particular feature, structure or characteristic described in connection with the embodiment is included in at least one embodiment of the present invention. Thus, appearances of the phrases "in one embodiment" or "in an embodiment" in various places throughout this specification are not necessarily all referring to the same embodiment, but may. Furthermore, the particular features, structures or characteristics may be combined in any suitable manner, as would be apparent to one of ordinary skill in the art from this disclosure, in one or more embodiments.

Similarly it should be appreciated that in the description of exemplary embodiments of the invention, various features of the invention are sometimes grouped together in a single embodiment, figure, or description thereof for the purpose of streamlining the disclosure and aiding in the understanding of one or more of the various inventive aspects. This method of disclosure, however, is not to be interpreted as reflecting an intention that the claimed invention requires more features than are expressly recited in each claim. Rather, as the following claims reflect, inventive aspects lie in less than all features of a single foregoing disclosed embodiment. Thus, the claims following the detailed description are hereby expressly incorporated into this detailed description, with each claim standing on its own as a separate embodiment of this invention.

Furthermore, while some embodiments described herein include some but not other features included in other embodiments, combinations of features of different embodiments are meant to be within the scope of the invention, and form different embodiments, as would be understood by those in the art. For example, in the following claims, any of the claimed embodiments can be used in any combination.

In the description provided herein, numerous specific details are set forth. However, it is understood that embodiments of the invention may be practiced without these specific details. In other instances, well-known methods, structures and techniques have not been shown in detail in order not to obscure an understanding of this description.

The present invention relates to the evaluation of the electrical isolation between a pulmonary vein and the heart by automated analysis of electrogram data recorded at the junction between the left atrium of the heart and the pulmonary vein, e.g. recorded during a radio-frequency ablation procedure. By such evaluation, a distinction can be made, in accordance with a decision algorithm, between the case where the electrogram data comprises both pulmonary vein potentials and far field potentials, e.g. where the pulmonary vein is not electrically isolated, and the case where the electrogram data contains only far field potentials, e.g. where the pulmonary vein is electrically isolated.

In one aspect, the present invention relates to a method for analysing electrophysiological data, e.g. electrocardiogram data. This method comprises obtaining at least one electrocardiogram recorded in a junction region between a pulmonary vein and a left atrium of the heart in a subject, e.g. obtaining a pre-recorded electrocardiogram characterising a time evolution of a biological electric field potential in a point near this junction region. The method further comprises determining a morphology classification representative of a waveform shape for the or each at least one electrocardiogram.

The method also comprises determining a first value, e.g. a first likelihood ratio, representative of a likelihood that the at least one electrocardiogram comprises a pulmonary vein potential component, in which this determining of the first value takes the morphology classification into account. The method further comprises generating a signal indicative for the detected presence of a pulmonary vein potential component in the electrocardiogram when the first value satisfies a first predetermined criterion, e.g. when the first value is greater than a predetermined likelihood threshold value, and generating a signal indicative for the detected absence of the pulmonary vein potential component when the first value satisfies a second predetermined condition, e.g. when the first value is less than a predetermined likelihood threshold value.

The method further comprises determining at least one morphological parameter indicative of a waveform feature of the or each at least one electrocardiogram, and determining a second value, e.g. a second likelihood ratio, e.g. a weighted likelihood ratio, representative of a likelihood that the at least one electrocardiogram comprises a pulmonary vein potential component, in which this determining of the second value takes into account the at least one morphological parameter and the morphology classification.

The method further comprises generating a signal indicative for the detected presence of the pulmonary vein potential component in the electrocardiogram when the second value satisfies a third predetermined criterion.

Referring to FIG. 1, a flow chart of an exemplary method 100 for analysing electrophysiological data according to embodiments of the present invention is shown. The method 100 comprises the first step of obtaining 102 at least one electrocardiogram recorded in a junction region between a pulmonary vein and a left atrium of the heart in a subject. For example, at least one electrocardiogram is obtained from at least one predetermined pulmonary vein from a subject recorded at a junction position between the at least one predetermined pulmonary vein and the left atrium of the heart of the subject. Obtaining 102 the at least one electrocardiogram may comprise obtaining such at least one electrocardiogram from a set of electrodes, e.g. may comprise the measuring of a plurality of electrocardiogram signals, the obtaining 102 may comprise receiving the electrocardiogram from a transfer medium, e.g. via a data carrier or via a data transmission network infrastructure.

Figure 2:
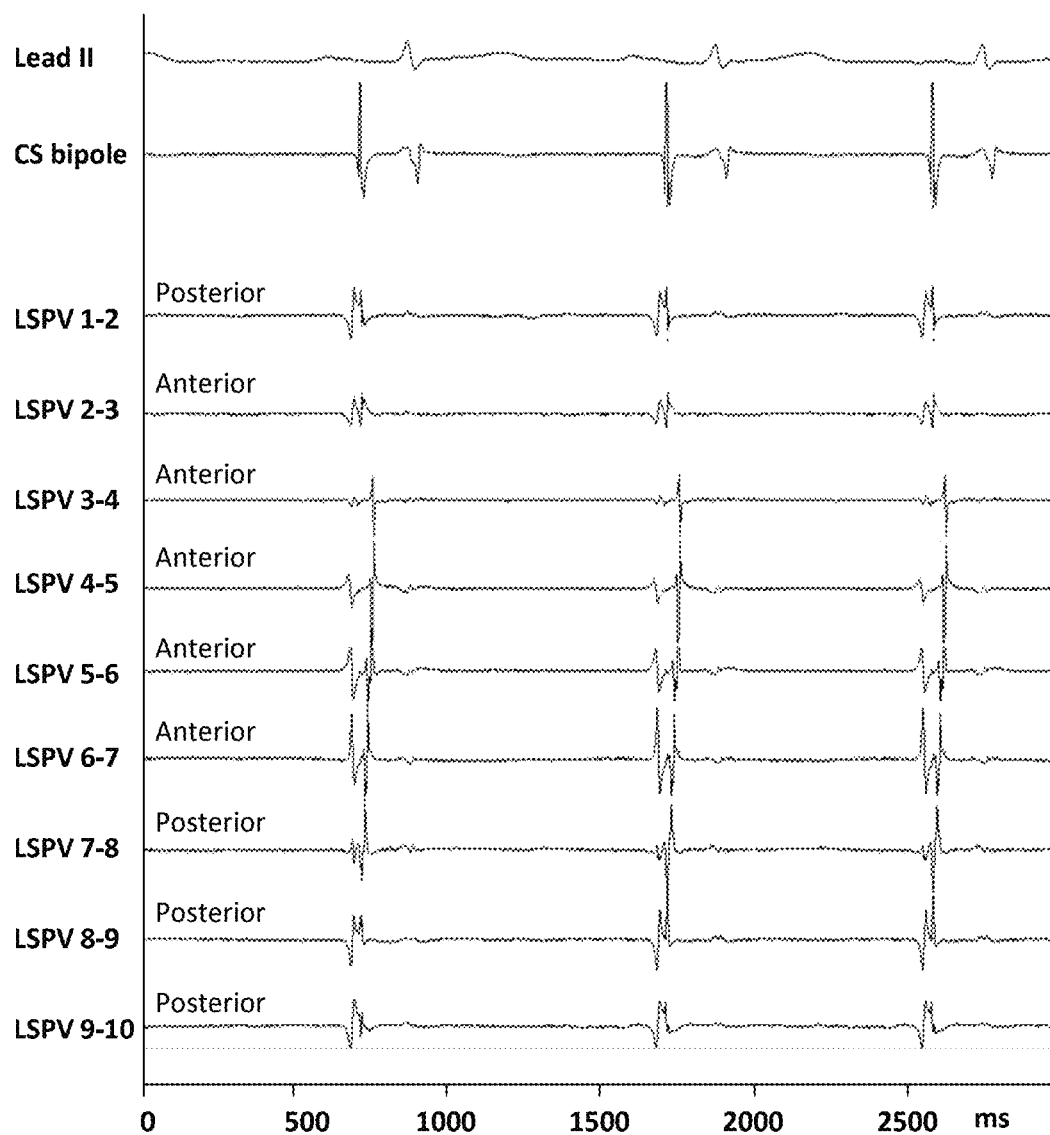
FIG. 2 shows a surface lead electrocardiogram (ECG), a proximal coronary sinus ECG and multi-electrode ECGs recorded at a junction position between the left superior pulmonary vein and the left atrium of the heart, the multi-electrode ECGs comprising a mixture of pulmonary vein potentials (PVP) and far field potentials (FFP), for illustrating aspects of embodiments of the present invention.
Figure 3:
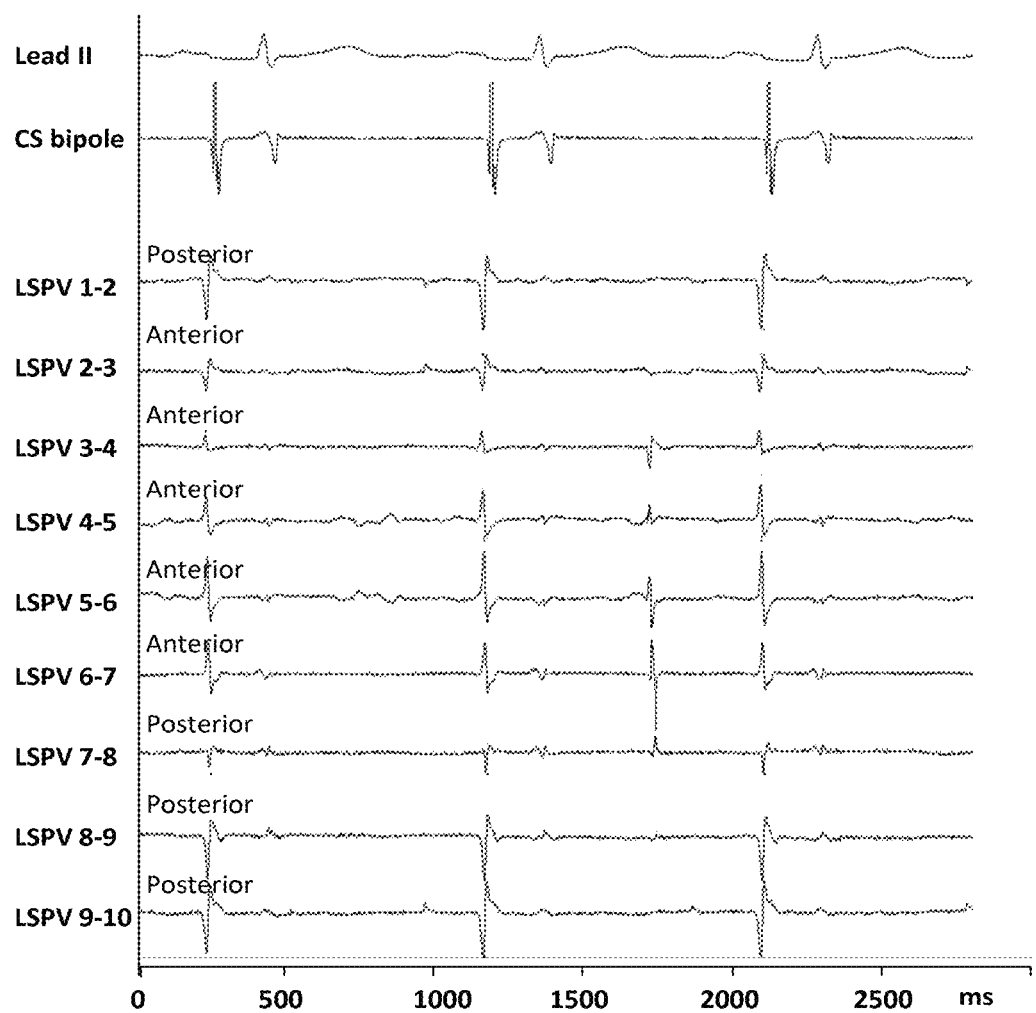
FIG. 3 shows a surface lead electrocardiogram (ECG), a proximal coronary sinus ECG and multi-electrode ECGs recorded at a junction position between the left superior pulmonary vein and the left atrium of the heart, the multi-electrode ECGs comprising only far field potentials (FFP), for illustrating aspects of embodiments of the present invention.

The at least one predetermined pulmonary vein may be one of: the left-superior pulmonary vein (LSPV), the right-superior pulmonary vein (RSPV), the left-inferior pulmonary vein (LIPV) or the right-inferior pulmonary vein (RIPV). The at least one electrocardiogram recorded at a junction position between the at least one predetermined pulmonary vein and the left atrium of the heart may be one or a plurality of electrocardiograms, each of the electrocardiograms being recorded at different positions at the junction between the at least one predetermined pulmonary vein and the left atrium of the heart. Such recording of a plurality of electrocardiograms may for instance be done using a multi-electrode catheter, such as for instance a circular catheter comprising multiple electrodes, e.g. a decapolar circular mapping catheter. FIG. 2 illustrates such a plurality of electrocardiograms LSPV 1-2, LSPV 2-3, . . . and LSPV 9-10 obtained with a decapolar circular catheter electrode for the left-superior pulmonary vein (LSPV) in a patient. Furthermore, a surface electrogram Lead II and a proximal coronary sinus electrocardiogram CS are shown for reference. In the electrocardiograms shown in FIG. 2, pulmonary vein potentials (PVP) and far field potentials (FFP) are present in a mixed state, indicative of the presence of an electrically conductive path between the left atrium and the LSPV vein. On the other hand, FIG. 3 illustrates a second plurality of electrocardiograms obtained under similar conditions in the same patient and for the same pulmonary vein LSPV after performing an isolating ablation procedure. After this pulmonary vein isolation (PVI), a PVP component in the electrocardiograms LSPV 1-2, LSPV 2-3, . . . and LSPV 9-10 is no longer present.

The method 100 may furthermore comprise preprocessing 101 the at least one electrocardiogram after obtaining 102 the at least one electrocardiogram recorded in the junction region by detecting, aligning and/or averaging of a plurality of atrial potentials corresponding to a plurality of heart beats in the or each at least one electrocardiogram. It is an advantage of embodiments according to the present invention that inter-beat variability and signal artefacts can be reduced by detecting, aligning and averaging multiple waveform portions corresponding to multiple heart beats. However, in advantageously simple embodiments, the method may comprise selecting of a single atrial potential, e.g. by manual selection or automatic detection, for example without requiring additional pre-processing and/or inter-beat averaging techniques.

Figure 4:
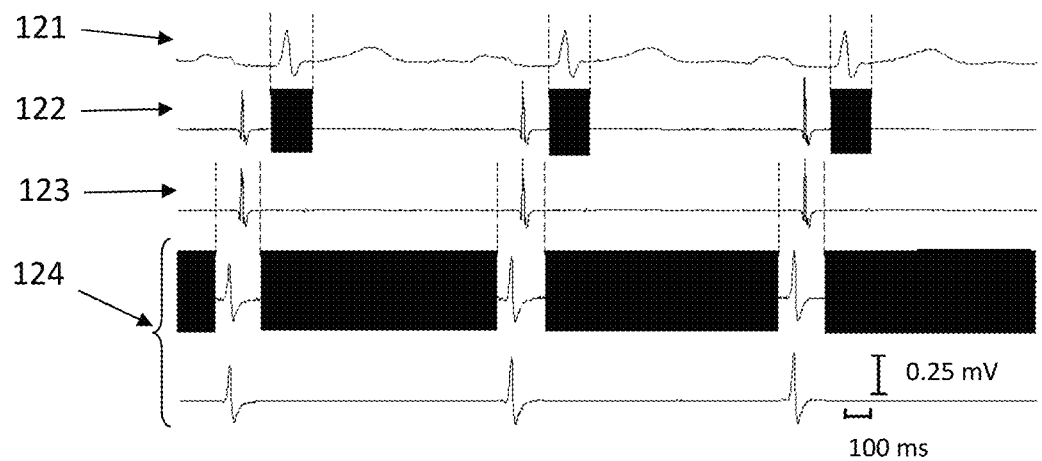
FIG. 4 illustrates the detection of atrial potentials in a preprocessing step in accordance with embodiments of the present invention.

FIG. 4 and FIG. 5 illustrate a pre-processing step 101, comprising a detection of the atrial potentials in the or each at least one electrocardiogram, in FIG. 4, and the alignment and averaging 125 of the detected atrial potentials in FIG. 5 for each at least one electrocardiogram. This detecting of the atrial potentials may for example comprise detecting QRS complexes 121 in a coregistered surface ECG Lead II electrocardiogram and blanking or masking 122 the time frames corresponding to the detected QRS complexes from a coregistered coronary sinus (CS) electrocardiogram. Thus, the atrial potentials corresponding to a plurality of heart beats may be identified 123 in the CS electrocardiogram. The identified time frames of the atrial potentials may then be selected 124 from the at least one electrocardiogram recorded in the junction region, such that a plurality of atrial potentials are detected in the or each at least one electrocardiogram, e.g. a plurality of left atrium-pulmonary vein (LA-PV) potentials are selected, extracted and/or indexed in the or each at least one electrocardiogram.

The method 100 further comprises determining 104 a morphology classification representative of a waveform shape for the or each at least one electrocardiogram. The morphology classification may for example be determined by assigning each waveform to one of a finite and discrete plurality of morphological classes, e.g. by determining the number of peaks and/or valleys present in the waveform, applying a template matching technique and/or performing a wavelet analysis. In embodiments which are advantageously easy to implement and robust, the morphology classification may be determined taking into account the number of peaks in the at least one electrocardiogram, e.g. determining the number of peaks in a pre-processed electrocardiogram obtained by averaging over a plurality of atrial potentials as explained hereinabove. Determining the number of peaks may be done by determining the number of peaks of each of the determined plurality of LA-PV potentials and taking the average therefrom or determining the number of peaks of the determined average LA-PV potential in the electrocardiogram or any other method considered suitable by the person skilled in the art. Peak detection may be performed using any peak detection algorithm considered suitable by the person skilled in the art. A detected peak may be considered valid, regardless of positive or negative polarity of the peak, if the amplitude of the peak is above a predetermined noise threshold, e.g. above the dynamic EGM noise threshold, and/or if the angle of the peak is less than a predetermined angle, e.g. if the degree of curvature of the local maximum is greater than a predetermined threshold, e.g. greater than 22.5 degrees. The morphology classification may comprise a selection from a predetermined set of candidate morphologies, e.g. comprising one or more of: "low voltage" classification, having no detected valid peaks, "monophasic" classification, having only one detected valid peak, "biphasic" classification, having two detected valid peaks, "triphasic" classification, having three detected valid peaks, "multiphasic" classification, having 4 or more peaks and "double potential" classification, having at least 2 valid detected peaks being separated by a predetermined isoelectric window. However, the morphology classification may also comprise a selection from a different set of candidate morphologies, such as classes determined by signal frequency characteristics, scale characteristics and/or combinations thereof, e.g. based on a wavelet decomposition. For example, the average potential of the aligned potentials shown in FIG. 5 can be classified as biphasic in a method according to embodiments of the present invention.

The method 100 further comprises determining 106 a first value representative of a likelihood that the at least one electrocardiogram comprises a pulmonary vein potential component, wherein this determining the first value takes the morphology classification into account. This first value may be determined by evaluating the prevalence of the detected morphology classification in a library of reference data obtained from electrocardiograms obtained under similar conditions from reference subjects containing a verified pulmonary vein potential component, and evaluating the prevalence of the detected morphology classification in a library of reference data obtained from electrocardiograms obtained under similar conditions from reference subjects showing a verified absence of a pulmonary vein potential component. Similar conditions may refer to the use of the same or the same type of electrocardiography catheter. Similar conditions may refer to the application to the same pulmonary vein, e.g. also relating to the left-superior pulmonary vein (LSPV), the right-superior pulmonary vein (RSPV), the left-inferior pulmonary vein (LIPV) or the right-inferior pulmonary vein (RIPV). Similar conditions may refer to electrogram data collected from the same anatomical position with respect to the pulmonary vein.

The method 100 according to embodiments of the present invention may comprise obtaining a hemisphere classification of the at least one electrocardiogram, e.g. a hemisphere classification may be performed based on the anatomical location where the at least one electrocardiogram has been recorded in relation to the pulmonary vein. For example, the hemisphere classification may be an assignment of an electrocardiogram to either "posterior" or "anterior", where this classification refers to an electrocardiogram recording in either the half of the vein more proximal to the anterior side of the body or the half of the vein more proximal to the posterior side of the body. It is an advantage of embodiments of the present invention that the specialization as function of an anatomical subregion, e.g. the hemisphere classification, can increase the accuracy of the method, e.g. by taking additional relevant data into account. Alternatively, in advantageously simple and fast methods according to embodiments of the invention, such specialization as function of the hemisphere classification may not be applied. The hemisphere classification may be manually provided by the user, e.g. selected, for the or each electrocardiogram, or may be automatically detected, e.g. by comparing the or each electrocardiogram to a reference template for each hemisphere class. Furthermore, embodiments of the present invention may also take a more detailed anatomical subregion classification into account, e.g. by dividing the pulmonary vein in four quadrants, e.g. anterosuperior, anteroinferior, posterosuperior, and posteroinferior.

A reference library for looking up the likelihood values may comprise prevalence data for a particular morphology detected by the morphology classification of the electrocardiogram data, relating to electrocardiograms comprising a verified pulmonary vein potential component on one hand and relating to electrocardiograms having an established absence of a pulmonary vein potential component. Furthermore, such reference library may contain data for distinguishing between the different pulmonary veins, e.g. may contain data entries specific to each of the left-superior pulmonary vein (LSPV), the right-superior pulmonary vein (RSPV), the left-inferior pulmonary vein (LIPV) and the right-inferior pulmonary vein (RIPV), and may comprise a further specialisation of the data entries in function of hemisphere classification, e.g. anatomical location within each pulmonary vein, e.g. may contain separate entries relating to posterior side electrograms and anterior side electrograms for each type of pulmonary vein.

For example, FIG. 7 illustrates an exemplary reference library for determining the first value. In this example, the reference library comprises observation counts grouped by the anatomical side of each pulmonary vein with respect to the anatomical anterior-posterior axis. Each such group comprises for each morphology classification that can be detected by the method two counts of observed reference cases having this morphology classification, one count for cases showing no PVP component and one count for cases showing a PVP component. The prevalence entries are depicted for respectively a "low voltage" classification, a "monophasic" classification, a "biphasic" classification, a "triphasic" classification, a "multiphasic" classification, and a "double potential" classification.

In a preferred embodiment, obtaining 102 at least one electrocardiogram recorded in a junction region between a pulmonary vein and a left atrium of the heart in a subject comprises obtaining a plurality of electrocardiograms recorded at different locations in this junction region. For example, the electrocardiograms may be recorded using a plurality of leads, e.g. pairs of adjacent leads, in a circular electrode catheter inserted into the junction region. Thus, for each of these electrocardiograms, a morphology classification is obtained. Determining 106 the first value representative of the likelihood that the at least one electrocardiogram comprises a pulmonary vein potential component, may comprise aggregating values associated with each morphology classification corresponding to the plurality of electrocardiograms. Referring to FIG. 8, an example of such determining the first value is shown. Here, for each electrocardiogram two observation count values are looked up in a reference library, e.g. as illustrated in FIG. 7. The morphological classification, the pulmonary vein at hand and the anatomical posterior or anterior location where the electrocardiogram is recorded in the vein, i.e. the hemisphere classification, may be used to look up these observation count values in the reference library. One count corresponds to a number of reference cases where PVP were observed for the specific combination of classification, vein and location, and the other count corresponds to a number of reference cases where no PVP could be observed for the specific combination of classification, vein and location.

Determining 106 the first value representative of the likelihood that the at least one electrocardiogram comprises a pulmonary vein potential component, may comprise aggregating values associated with each morphology classification corresponding to the plurality of electrocardiograms. For example, this first value may be a morphology ratio $(A-B)/(A+B)$ where A is the sum of the observation counts associated with presence of PVP and B is the sum of the observation counts associated with the absence of PVP.

Although determining the first value is described hereinabove as a process of looking up a pair of observation counts and aggregating these into a ratio, it will be apparent to the person skilled in the art that other methods for determining a first value indicative of a likelihood of the presence of PVP in the recorded at least one electrocardiogram given the classification may be also suitable. For example, a lookup table may define a list of conditional, marginal and/or joint probabilities for at least the PVP presence indicator and the classification variable.

The method 100 further comprises generating 111 a signal indicative for the detected presence or detected absence of the pulmonary vein potential component when the first value respectively satisfies a first predetermined condition or a second predetermined condition, e.g. when the first value is greater than a first threshold value or less than a second threshold value. The signal indicative for the detected presence or absence of a PVP component may also indicate sufficient electrical isolation of the pulmonary vein from the left atrium, e.g. sufficient to avoid atrial fibrillation being triggered from the pulmonary vein.

For example, if the first value, e.g. the morphology ratio described hereinabove, is above or below certain pre-determined cut-offs, the method may conclude with a signal indicating respectively the presence or absence of pulmonary vein potentials in the recorded electrocardiograms. However, if the first value lies in between the 2 cut-offs, no signal may be generated, e.g. the result is inconclusive.

It is an advantage of embodiments of the present invention that a robust first detection based on a morphological classification may be combined with a second detection step based on further parameters when this first detection is inconclusive. The first detection step may be inconclusive when the first value satisfies neither the first predetermined condition nor the second predetermined condition.

The method 100 further comprises determining 108 at least one morphological parameter indicative of at least one waveform feature for the or each at least one electrocardiogram. In a preferred embodiment of the present invention, the step of determining 108 the at least one morphological parameter, and the consecutive steps of determining 110 a second likelihood value and generating 112 a signal may be only performed when the first value satisfies neither the first predetermined condition nor the second predetermined condition, e.g. when the first value did not provide conclusive evidence in support of either the presence or absence of PVP in the recorded at least one electrocardiogram. It is an advantage of such embodiments that the presence of pulmonary vein potentials may be efficiently detected.

Determining 108 at least one morphological parameter indicative of at least one waveform feature may comprise determining at least one morphological parameter of one or more of the determined LA-PV potentials and averaging these or determining at least one morphological parameter of the determined average LA-PV potential. The at least one morphological parameter may comprise a peak-to-peak amplitude, e.g. the amplitude difference between the maximal positive and negative peaks. The at least one morphological parameter may comprise the maximal slope, e.g. the absolute value of the maximal positive or negative slope of the curve. The at least one morphological parameter may comprise the minimal slope, e.g. the minimal positive or negative slope of the curve. The at least one morphological parameter may comprise the sharpest peak-angle, e.g. the minimal angle between the upstrokes and downstrokes of the peaks of the curve. The at least one morphological parameter may comprise the time to coronary sinus, e.g. the time difference between the onset of activation of the coronary sinus potential and the onset of activation of LA-PV potential of the obtained electrocardiogram. The at least one morphological parameter may thus comprise one or more of the following parameters: peak-to-peak amplitude, maximal slope, minimal slope, sharpest peak angle or time to coronary sinus. The at least one morphological parameter may also comprise one or more of the following parameters: the duration of the potential waveform, the flattest peak angle, the first slope of the potential waveform, the last slope of the potential waveform, a center of mass or center of energy measure and/or a cumulative power.

For example, FIG. 6 illustrates the determining of such morphological parameters. In this example, the determined peak-to-peak amplitude 1 was 0.46 mV, the maximal slope 2 was 0.061 mV/ms, the minimal slope 3 was 0.008 mV/ms, the minimal peak angle 4 was 3 degrees and the time to CS 5 was −43 ms.

The method 100 further comprises determining 110 a second value representative of the likelihood that the at least one electrocardiogram comprises a said pulmonary vein potential component, wherein this determining of the second value takes the at least one morphological parameter and the morphology classification into account. The second value may be a weighted statistical parameter based on a comparison between the at least one morphological parameter and a corresponding range or threshold. Such range or threshold may be selected as function of the morphology classification and the pulmonary vein, e.g. a range or threshold may be selected specific to the morphological parameter, the morphology classification, the pulmonary vein being studied and the anatomical location in the vein where the electrocardiogram is recorded, i.e. the hemisphere classification.

The method 100 further comprises generating 112 a signal indicative for the detected presence of the pulmonary vein potential component when the second value satisfies a third predetermined criterion. The second value, e.g. a weighted likelihood parameter, may be compared to the third predetermined criterion, e.g. a weighted likelihood parameter threshold. Such criterion may be selected from a list of suitable criteria as function of the pulmonary vein at hand, may differ depending on whether, for example, the LIPV or RSPV is being analysed.

The method 100 may also comprise generating a signal indicative for the detected absence of the pulmonary vein potential component when the second value satisfies a fourth predetermined criterion. The method 100 may also comprise generative a signal indicative of an inconclusive determination of the presence or absence when neither one of the first criterion, the second criterion, the third criterion and the fourth criterion is satisfied.

Referring to FIG. 9, an example of determining the first and second value is shown. Here, for each electrocardiogram two observation count values are looked up in a reference library, e.g. as also illustrated in FIG. 8. However, here the first value does not satisfy the first or second criterion, such that the first stage of the method is inconclusive. For each electrocardiogram, a plurality of morphological parameters is tested, in which each parameter may be tested to lie within a range specific to the morphological classification, the pulmonary vein and/or the hemisphere classification, e.g. the anatomical location in the vein. The number of morphological parameters satisfying the corresponding testing range may be added and the components used to obtain the first value may be reweighted by these counts and summed to obtain the second value, as illustrated in FIG. 9.

A method according to embodiments enables a direct assessment of the electrical isolation of a pulmonary vein by analyzing the electrograms recorded at the PV-LA junction. Such method may be automated, e.g. be performed by a computing device. For example, a method according to embodiments may use an algorithm to characterize the morphology, e.g. to determine a morphologic class of the electrocardiogram, and a set of morphological parameters, e.g. peak-to-peak amplitude, maximal slope, minimal slope, peak angle and duration to coronary sinus, of the LA-PV electrograms. In a reference library, each of the four pulmonary veins (right superior, right inferior, left superior, and left inferior) and their hemispheres (anterior and posterior) may be defined by a unique set of morphology ratios and parameters cut-offs. For example, the morphology "biphasic" in the left superior PV (anterior hemisphere), may have a ratio of 15/27. The same morphology in the left superior PV (posterior hemisphere), may have a ratio of 19/30.

To detect if an LA-PV electrogram contains both PVP and FFP or only FFP, the method may use a step wise approach. In the second step, the parameters matching the template may act as a weight factor to modify the morphology ratio. A library for template matching may be constructed from previously recorded observations.

In another aspect, the present invention relates to a computer program stored on a computer readable medium configured to carry out a method according to embodiments of the present invention.

Figures 10, 11:
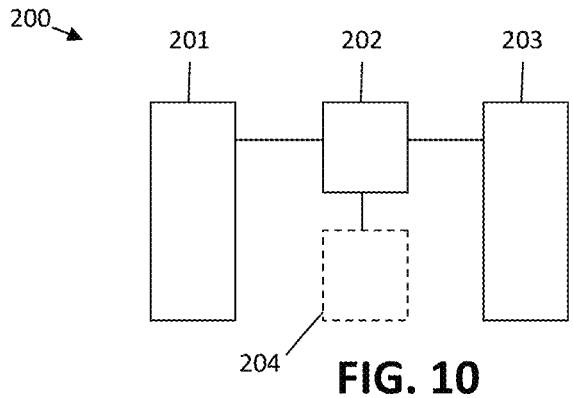
FIG. 10 illustrates a device according to embodiments of the present invention.
FIG. 11 illustrates the determining of the first value in accordance with embodiments of the present invention, applied to data recorded at a left inferior pulmonary vein after performing an electrically isolating ablation procedure.
Figure 12:
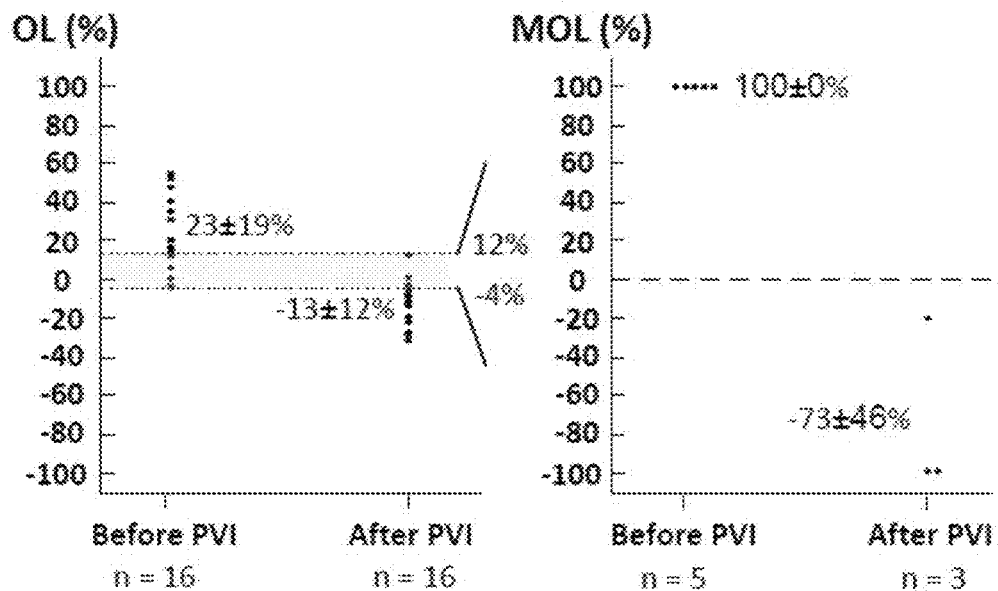
FIG. 12 shows the first value in the form of an ordinary likelihood (OL), exemplary first and second criteria in the form of threshold values, and the second value in the form of a modified ordinary likelihood (MOL) in accordance with embodiments of the present invention, for the left superior pulmonary vein.
Figure 13:
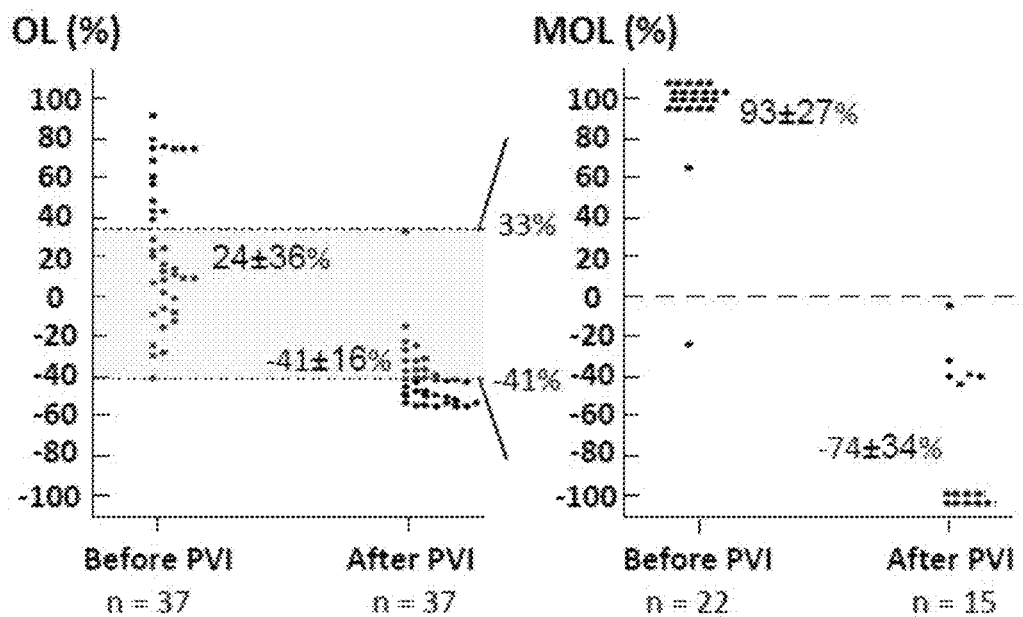
FIG. 13 shows the first value in the form of an ordinary likelihood (OL), exemplary first and second criteria in the form of threshold values, and the second value in the form of a modified ordinary likelihood (MOL) in accordance with embodiments of the present invention, for the right superior pulmonary vein.
Figure 14:
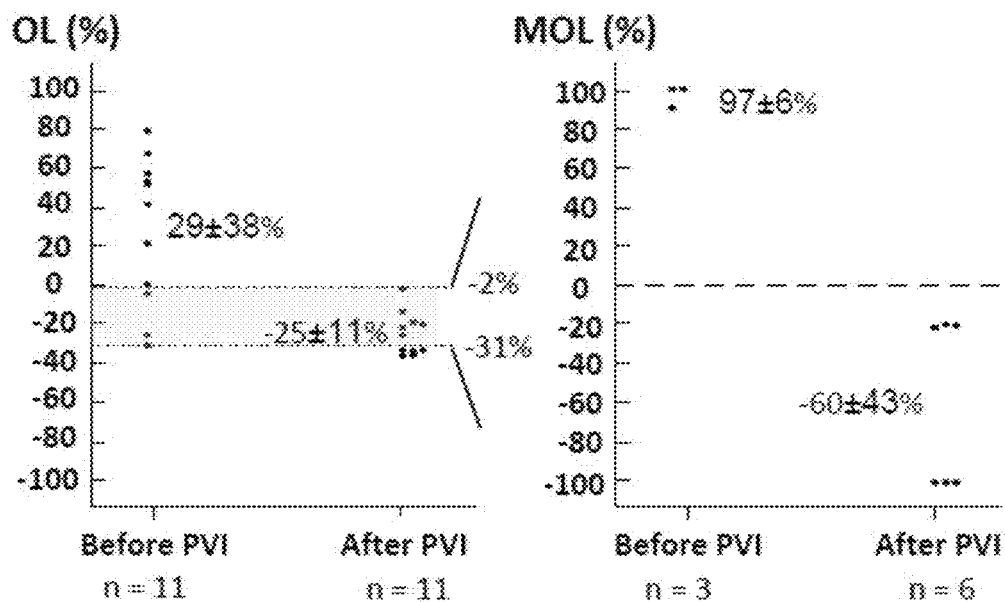
FIG. 14 shows the first value in the form of an ordinary likelihood (OL), exemplary first and second criteria in the form of threshold values, and the second value in the form of a modified ordinary likelihood (MOL) in accordance with embodiments of the present invention, for the left inferior pulmonary vein.
Figure 15:
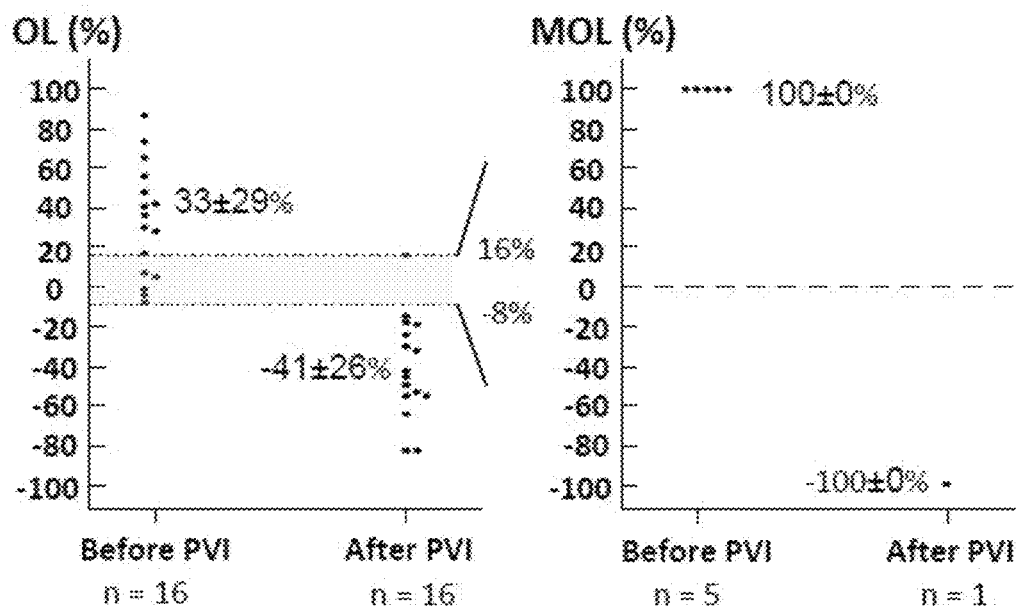
FIG. 15 shows the first value in the form of an ordinary likelihood (OL), exemplary first and second criteria in the form of threshold values, and the second value in the form of a modified ordinary likelihood (MOL) in accordance with embodiments of the present invention, for the right inferior pulmonary vein.

The present invention also relates to a device for analyzing electrophysiological data, e.g. a computing device executing a computer program according to the second aspect. An exemplary device 200 for analysing electrophysiological data according to embodiments of the present invention is shown in FIG. 10.

Such device 200 comprises an input means 201 for inputting at least one electrocardiogram recorded in a junction region between a pulmonary vein and a left atrium of the heart in a subject, e.g. the device may comprise connection means for receiving an input signal from an ECG electrode array. Thus, the input means 201 may be adapted for recording a plurality of electrocardiograms from the pulmonary vein, such that each of the plurality of electrocardiograms is recorded at a plurality of different junction positions between the pulmonary vein and the left atrium of the heart of the subject. However, the input means 201 may also comprise a reader for a data carrier medium, e.g. a drive for removable disks or an optical disc reader, or an interface for receiving the at least one electrocardiogram via a data transfer network.

The device 200 further comprises a processing means 202 adapted for determining a morphology classification representative of a waveform shape for the or each at least one electrocardiogram, and adapted for determining a first value representative of a likelihood that the at least one electrocardiogram comprises a pulmonary vein potential component. This determining of the first value takes the morphology classification into account, for example as described hereinabove in relation to the method according to the present invention.

The device also comprises an output means 203 for generating a signal indicative for the detected presence of the pulmonary vein potential component when the first value satisfies a first predetermined condition and a signal indicative for the detected absence of the pulmonary vein potential component when the first value satisfies a second predetermined condition.

The processing means 202 is furthermore adapted for determining at least one morphological parameter indicative of at least one waveform feature for the or each at least one electrocardiogram and determining a second value representative of the likelihood that the at least one electrocardiogram comprises the pulmonary vein potential component, wherein this determining of the second value takes the at least one morphological parameter and said morphology classification into account.

The output means 203 is furthermore adapted for generating a signal indicative for the detected presence of the pulmonary vein potential component when the second value satisfies a third predetermined criterion.

The device 200 may furthermore comprise a storage means 204 for storing previously recorded prevalence information for the morphological classification, and the processing means 202 may be adapted for determining the first value taking the previously recorded prevalence information into account.

The processing means 202 may be adapted for preprocessing the at least one electrocardiogram by detecting, aligning and/or averaging of a plurality of atrial potentials corresponding to a plurality of heart beats in the or each at least one electrocardiogram, for example as described hereinabove.

The device according to embodiments of the present invention may be adapted for implementing any of the steps of the method according to the present invention as described above.

The processing means 202 may for instance furthermore be adapted for determining the morphology classification for the or each of the plurality of electrocardiograms.

The processing means 202 may furthermore be adapted for determining a number of peaks above a predetermined noise threshold and determining the morphology classification may take into account the determined number of peaks.

The processing means 202 may furthermore be adapted for determining an angle between an upstroke and a downstroke of a detected peak and comparing the determined angle with a predetermined angle, wherein the processing means is adapted for determining the morphology classification taking into account said comparing.

The processing means may furthermore be adapted for selecting one of a low voltage class, a monophasic peak class, a biphasic peak class, a triphasic peak class and multiphasic peak class when determining the morphology classification.

The processing means may furthermore be adapted for determining at least one out of a peak-to-peak amplitude, a maximum slope, a minimal slope, a sharpest peak angle and a time to coronary sinus when determining the at least one morphological parameter.

The processing means may furthermore be adapted for determining a hemisphere classification for the or each at least one electrocardiogram.

The input means may furthermore be provided for inputting a hemisphere classification for the at least one electrocardiogram.

The processing means may furthermore be adapted for taking said hemisphere classification into account when determining the first and/or second value.

Hereinbelow, examples of embodiments of the present invention and results relating thereto are described for illustrative purposes. It is to be noticed that specific steps or device features used are not limiting for embodiments of the present invention, but merely describe the way the results are obtained for the present examples. Catheter-based pulmonary vein (PV) ablation is a successful therapeutic strategy in patients with drug-resistant and symptomatic recurrent atrial fibrillation (AF). Complete electrical PV isolation (PVI) is commonly considered to be an essential endpoint for a successful outcome of the procedure. However, verification of PVI can be challenging because bipolar electrograms (EGM) recorded by circular mapping catheters (CMC) at the left atrium-pulmonary vein (LA-PV) junction may contain local PV potentials (PVP) and far-field potentials (FFP).

In this example, data were collected from 61 patients undergoing electroanatomical mapping (EAM)-guided first circumferential PVI for drug-refractory, symptomatic and recurrent AF (58±9 years, 78% males, 80% paroxysmal AF, no structural heart disease). For characterization of LA-PV potentials, 61 patients were studied. From these patients, only the following PV recordings were selected: 1) where PV automaticity was observed after ablation (unambiguous proof of isolation) and 2) where baseline PV recording was available with the CMC at the same position as after PVI. As such paired analysis was performed in 160 PV recordings: 16 left superior PV (LSPV), 11 left inferior PV (LIPV), 37 right superior PV (RSPV), and 16 right inferior PV (RIPV). This resulted in a library of 1440 LA-PV electrograms (9 bipoles per PV recording). The library (n=1440) was used for the characterization of the LA-PV potentials and development of an algorithm to verify PV isolation in accordance with embodiments of the present invention.

For prospective validation of the algorithm, recordings were collected from another 20 patients. The recordings comprised 43 PVs before isolation (11 LSPV, 7 LIPV, 18 RSPV, 7 RIPV) and 47 PVs after isolation (11 LSPV, 7 LIPV, 18 RSPV, 11 RIPV).

For the data collection and ablation treatment, a decapolar catheter was positioned in the coronary sinus (CS). After transseptal puncture, 3D reconstruction of the LA was made by an EAM system, using an irrigated-tip ablation catheter (NaviStar ThermoCool, Biosense Webster). The ablation procedure consisted of encircling ipsilateral PVs as a single unit by a continuous circular lesion set during sinus rhythm. Except for the anterior aspect of the left PVs, lesions were created 10 to 20 mm outside of the ostia as defined from the 3D map. The continuous lesion set was made by point-by-point radiofrequency (RF) applications (20 to 35 W, 30 to 60 s, max 42° C., irrigation 20 ml/min). The PVs were continuously assessed for electrical disconnection using a decapolar (2 mm electrodes, spacing 8 mm) CMC (Lasso, 2515 variable catheter, Biosense Webster) placed at the LA-PV junction. The endpoint for ablation was LA-PV entry block, defined as elimination of all PV potentials or PV automaticity (unambiguous proof of entry block).

Intracardiac EGMs were recorded using the Bard EP system (Boston Scientific, Natick, Mass., USA) at a sampling rate of 1000 Hz and filtered 10-250 Hz. For each selected PV, 3 second recordings were extracted from the surface ECG (lead II), the proximal bipole of the CS, and 9 bipolar EGMs from the CMC (1-2, 2-3, 3-4 . . . ). Each CMC bipole was assigned a hemisphere (anterior or posterior) based upon its anatomical location determined from the EAM.

The EGMs were offline preprocessed in Matlab (The MathWorks, Inc., Natick, Mass., USA). First, atrial potentials were detected on the CS electrogram (using a peak detection algorithm) to determine the atrial activation window of interest. Second, non-atrial potentials were blanked from the LA-PV electrogram of interest. Third, LA-PV potentials in the LA-PV electrogram were detected using a peak detection algorithm. Then, all detected LA-PV potentials (ranging from 2 to 6 beats) were time aligned (using the maximal positive or negative peak) and averaged into one LA-PV potential.

Custom Matlab software was used to determine the type of LA-PV potential based on the number of detected peaks. A local maximum was considered a valid peak (regardless of polarity) if the amplitude was above the dynamic EGM noise threshold and if the degree of curvature of the local maximum was more than 22.5 degrees. The LA-PV potential was algorithmically defined as: 1) low voltage (no peaks), 2) monophasic (one peak), 3) biphasic (two peaks), 4) triphasic (three peaks), 5) multiphasic (4 or more peaks), or 6) double potential (in the presence of at least 2 peaks separated by an iso-electric window of 25 ms). Analysis was performed for all EGMs (n=1440). To compare typology before and after PVI, results were summarized per PV and hemisphere.

Custom Matlab software was used to calculate five numerical parameters of the LA-PV potential for every EGM except for low voltage: 1) peak-to-peak amplitude, defined as the amplitude difference between the maximal positive and negative peaks; 2) maximal slope: to identify the maximal slope within the LA-PV potential, we calculated the average dv/dt for each upstroke and downstroke of the peak(s). The maximal slope was defined as the maximal average dv/dt; 3) minimal slope, defined as the minimal average dv/dt; 4) sharpest peak, defined as the minimal angle between the upstroke and downstroke of the peak(s). Analysis was performed for each EGM (n=1440). To compare the parameters before and after PVI, results were summarized per PV, hemisphere, and type.

Vein-dependent prevalence of a given type before and after PVI can be used to differentiate non-isolated from isolated PVs, as is illustrated by embodiments of the present invention. Therefore, for each PV recording (n=160) the overall likelihood (OL) that the PV (still) contains PVPs. OL (ranging from -100% to +100%) was used as the first step in the algorithm and was calculated as:

$$\frac{\sum_{i=1}^{9} PrevalenceBefore_{(i)} - \sum_{i=1}^{9} PrevalenceAfter_{(i)}}{\sum_{i=1}^{9} PrevalenceBefore_{(i)} + \sum_{i=1}^{9} PrevalenceAfter_{(i)}} \times 100$$

where i is the number of bipole. PV- and type-dependent cutoff values in parameters specific for LA-PV potentials before and after PVI can be used to differentiate non-isolated from isolated PVs, as illustrated by embodiments of the present invention. For this, the number of specific parameters was used as a weighing factor for the prevalence of that type before and after PVI. Therefore, for each PV the modified overall likelihood (MOL) that the PV (still) contains PVPs was determined. MOL (ranging from -100% to +100%) was used as the second step in the algorithm and was calculated as:

$$\frac{\sum_{i=1}^{9} ModifiedPrevalenceBefore_{(i)} - \sum_{i=1}^{9} ModifiedPrevalenceAfter_{(i)}}{\sum_{i=1}^{9} ModifiedPrevalenceBefore_{(i)} + \sum_{i=1}^{9} ModifiedPrevalenceAfter_{(i)}} \times 100$$

where i is the number of bipole. In case the LA-PV potential did not have any specific type-dependent parameters, MOL was equal to OL value.

The overall accuracy of the two-step algorithm to differentiate non-isolated from isolated PVs was prospectively evaluated in 20 patients (dataset of 90 PV recordings). In the exemplary results presented hereinbelow, continuous data are presented as mean±standard deviation. Significant difference in means between groups was calculated using Student's t-test. A p value of <0.05 was considered statistically significant.

Overall (n=1440) before PVI, there was a higher prevalence of triphasic (22±5% vs. 11±13%, p=0.036), multiphasic (26±7% vs. 3±3%, p<0.001), and double potentials (11±5% vs. 2±1%, p<0.001) as compared to after PVI. Vice versa, after PVI there was a higher prevalence of low voltage (10±7% vs. 36±15%, p<0.001), and monophasic potentials (13±4% vs. 27±9%, p=0.001). The prevalence of biphasic potentials was not significantly different before and after PVI (18±4% vs. 21±9%, N.S).

The difference in typology before and after PVI was also compared per PV and hemisphere. Before PVI, there was high prevalence of triphasic (n=4, 24%), multiphasic (n=4, 24%), and double potentials (n=3, 18%), whereas after PVI there was a shift towards more low voltage (n=7, 41%) and monophasic potentials (n=6, 35%). The overall results, for the RSPV anterior (37 PVs, 340 potentials) show a shift in the prevalence of types before and after PVI (low voltage: 26% to 53%, monophasic: 15% to 33%, triphasic: 17% to 1%, multiphasic: 14% to 0%, and double potentials: 15% to 3%). A similar shift was observed for the other PVs and hemispheres: the majority of potentials before PVI were triphasic, multiphasic, and double potentials (except for RSPV anterior and LIPV anterior), whereas after PVI, the majority of potentials were low voltage, monophasic, and biphasic.

Overall (n=1440) and independent of the type of potential, when comparing before PVI to after PVI, a higher peak-to-peak amplitude (0.97±0.21 vs. 0.35±0.23 mV, p<0.0001), a higher maximal slope (0.179±0.033 vs. 0.071±0.029 mV/ms, p<0.0001), a higher minimal slope (0.030±0.003 vs. 0.024±0.002 mV/ms, p=0.0003), and a sharper peak (1.82±0.26 vs. 3.45±0.85 degrees, p=0.0015) were observed. Despite the significant differences, all parameters showed a large overlap in range before and after PVI. The difference in the amplitude, slopes, and peak-angle before and after PVI per PV, hemisphere, and type were also compared. A representative example of a triphasic potential recorded at the posterior hemisphere of the LSPV before and after PVI is given in FIG. 5 (top left panel). Compared to the triphasic potential after PVI, the triphasic potential before PVI shows a higher voltage (2.69 vs. 0.73 mV), a steeper slope (0.63 vs. 0.05 mV/ms), and a sharper angle (0.4 vs. 3 degrees).

For example, using these results, cutoffs specific for LA-PV potentials in the LSPV posterior hemisphere before PVI may be determined: 1) monophasic: maximal slope >0.05 mV/ms, minimal slope >0.05 mV/ms, 2) biphasic: amplitude >1.72 mV, maximal slope >0.25 mV/ms, minimal slope >0.08 mV/ms, angle <1 degrees, 3) triphasic: amplitude >1.78 mV, maximal slope >0.18 mV/ms, minimal slope >0.04 mV/ms, peak-angle <1 degrees, 4) multiphasic: amplitude >1.85 mV, maximal slope >0.28 mV/ms, minimal slope >0.03 mV/ms, peak-angle <1 degrees, and 5) double potentials: amplitude >0.21 mV, maximal slope ≥0.08 mV/ms, minimal slope >0.01 mV/ms, peak-angle ≤2 degrees.

Vice versa, the following cutoffs were determined as suitable thresholds specific for LSPV anterior recordings after PVI: 1) monophasic: maximal slope <0.06 mV/ms, minimal slope <0.03 mV/ms, 2) biphasic: amplitude <0.14 mV, maximal slope <0.04 mV/ms, minimal slope <0.01 mV/ms, 3) triphasic: no specific parameters, 4) multiphasic: no specific parameters, and 5) double potentials: amplitude ≤0.15 mV, maximal slope ≤0.04 mV/ms, peak-angle ≥4 degrees. When compared per type, all parameters showed less overlap in range before and after PVI. Again, per-type-analysis allowed identification of cutoff values specific for LA-PV potentials either recorded before or after PVI.

Two representative PV recordings with their overall likelihood (OL) calculation are given in FIG. 8 and FIG. 11. FIG. 8 shows a recording from the RSPV before isolation. Automated typology indicates triphasic potentials in EGMs 1-2 and 9-10, multiphasic potentials in EGMs 2-3, 3-4, 4-5, and 5-6, biphasic potentials in EGMs 6-7 and 8-9, and double potentials in EGM 8-9. Next to the type of potential, the reported prevalence is indicated, based on the library of measurements discussed hereinabove, for that specific type for that given PV and hemisphere before and after isolation. As such, the OL that the recording contains PVP is calculated to be +75%. In FIG. 11, a recording from the LIPV after PVI is shown. Now the automated typology and calculation of prevalence generates an OL of −35%.

In FIG. 12 to FIG. 15, the OL values before and after PVI are plotted for respectively LSPV, RSPV, LIPV and RIPV. The mean OL was higher before PVI than after PVI (LSPV: 23±19% vs. −13±12%, RSPV: 24±36% vs. −41±16%, LIPV: 29±38% vs. −25±11%, and RIPV: 33±29% vs. −41±26%, p<0.0001 for all). Despite the significant difference, there was considerable overlap of OL value before and after PVI in 60 out of 160 PVs (38%, shaded areas). On the other hand, in 62% of PVs, the following OL cutoffs were specific for PV recordings before and after PVI respectively: In LSPV, OL>+12% and <−4%; in RSPV, OL>+33% and <−41%; in LIPV, OL>−2% and <−31%; in RIPV, OL>+16% and <−8%. These specific cutoffs were used in the first step of the two-step algorithm to differentiate non-isolated from isolated PVs. As such, the RSPV recording in FIG. 8 was identified as non-isolated PV (OL=+75%>+33%) whereas the LIPV recording in FIG. 11 was identified as an isolated PV (OL=−35%<−31%).

For those PV recordings with OL values in the overlapping range, indicated in FIG. 12 to FIG. 15, the MOL was calculated. Representative examples of PV recordings with intermediate OL values, together with their MOL values, are given in FIG. 9 and FIG. 16. Although the LSPV recording in FIG. 9 was recorded before PVI, the OL was only −4% (non-conclusive first step). This was due to the presence of mainly triphasic potentials which occur equally or even more in isolated PVs. Subsequent analysis of type-dependent parameters revealed that the LA-PV potential in EGM 1-2 (multiphasic with amplitude=2.7 mV and max. slope=0.4 mV/ms), EGM 4-5 (triphasic with max. slope=0.22 mV/ms), and EGM 5-6 (triphasic with amplitude=2.69 mV, max. slope=0.63 mV/ms, and peak-angle=0.4 degrees) had parameters specific for non-isolated PVs. No parameters specific for isolated PVs were identified. As a result, MOL value is +100%.

Figures 16, 17:
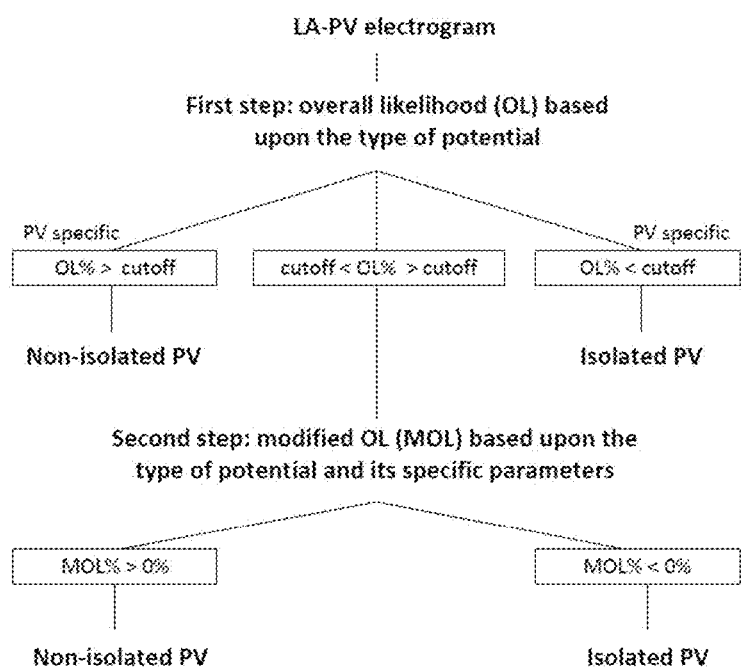
FIG. 16 illustrates the determining of the first and second value in accordance with embodiments of the present invention, applied to data recorded from a right inferior pulmonary vein after successfully performing an electrically isolating procedure.
FIG. 17 shows an exemplary flow diagram in accordance with embodiments of the present invention.

In FIG. 16, a recording from an isolated RIPV is plotted. The OL of +16% was indecisive due to the presence of mainly triphasic and multiphasic potentials. Type-dependent analysis revealed that the LA-PV potential in EGM 1-2 (biphasic with amplitude=0.1 mV), EGM 2-3 (biphasic with amplitude=0.17 mV, min. slope=0.009 mV/ms, peak-angle=7 degrees), and EGM 9-10 (monophasic with peak-angle=15 degrees) had parameters specific for isolated PVs. As a result MOL value is −100%.

In FIG. 12 to FIG. 15, for each intermediate OL value the MOL was also plotted. Overall, the modified OL ranged between −100% and +100%. The mean modified OL was higher before than after PVI (LSPV: 100±0% vs. −73±46%, RSPV: 93±27% vs. −74±34%, LIPV: 97±6% vs. −60±43%, RIPV: 100±0% vs. −100±0%, p<0.0001 for all). In contrast to OL, there was no overlap in the MOL value before and after PVI. A MOL value of 0% was used as a cutoff in the second step of the algorithm to differentiate non-isolated from isolated PVs (MOL>0% for isolated PVs and <0% for non-isolated PVs).

An exemplary flowchart of a two-step algorithm in accordance with embodiments of the present invention is shown in FIG. 17. The accuracy of this two-step algorithm was evaluated prospectively (20 patients) in a dataset of 90 PV recordings (unpaired analysis of 43 before and 47 after PVI). The algorithm accurately identified PVs as non-isolated (still containing PVP) with 100% sensitivity and 87% specificity (accuracy=93%, precision=88%). The algorithm showed 100% sensitivity and 91% specificity in LSPV recordings, 100% sensitivity and 86% specificity in LIPV recordings, 100% sensitivity and 89% specificity in RSPV recordings, and 100% sensitivity and 82% specificity in RIPV recordings.

The algorithm differentiated 65 out of 90 PVs in the first step (overall=72%, LSPV=77%, RSPV=64%, LIPV=64%, and RIPV=89%), of which, all were correctly classified except for 1 LIPV. In the second step (n=25, 28%), 20 PVs were correctly classified, whereas 5 PVs were misclassified (as containing PVP although proven isolated in LSPV=1, RSPV=2, and RIPV=2). These misclassified PVs were not characterized by any type-dependent specific parameters (i.e. MOL value was equal to OL value).

Thus, in the present example, an algorithmic characterization of 1440 left atrial-pulmonary vein bipolar electrograms was demonstrated, recorded by a circular mapping catheter during sinus rhythm before and after PVI (library of vein-specific types and parameters). Based upon this library, an automated and robust algorithm was presented to automatically differentiate between non-isolated and isolated PVs (93% accuracy).

Conventionally, PV isolation is verified by visual interpretation of (changes in) EGMs recorded by a circular multi-electrode catheter positioned at the LA-PV junction. Assessment of PVI (absence of PVP) however, remains challenging as FFP are recorded at the LA-PV junction before and after PVI. FFP originate from electric activation of structures adjacent to the right PVs (superior vena cava and posterior wall) and lateral PVs (LA appendage and low lateral LA wall). To improve accuracy in differentiating PVP from FFP, pacing maneuvers can be used. Alternatively, unipolar EGMs can been used to differentiate PVP from FFP. In the presence of PVP (i.e. before PVI), the unipolar EGM recorded on the ablation catheter may have the same morphology as the adjacent EGM recorded on the CMC. Nevertheless, assessment of PVI remains ambiguous. As such, an objective and accurate method for identification of PVP and FFP can be considered as advantageous.

A library of EGMs before (PVP+FFP) and after PVI (FFP) was constructed. For each vein and hemisphere, the morphology type and its distribution were determined algorithmically. This library of EGMs per PV and hemisphere can be used as a template to guide visual interpretation of PVI. Before PVI, due to aliasing of PVP and FFP, the EGM complex was observed to contain a larger number of peaks (triphasic, multiphasic, and double potentials), whereas EGM recorded after unambiguous PVI (FFP only) were characterized by low voltage, monophasic, and biphasic potentials. Additionally, for each vein, hemisphere, and type of EGM, the amplitude, maximal slope, minimal slope, and peak-angle were determined. Differences in LA-PV EGM amplitude and slopes before and after PVI were in line with prior reports (roughly before PVI>1 mV and >0.15 mV/ms whereas after PVI<0.5 mV and <0.1 mV/ms). A sharper peak in the LA-PV EGM before PVI (1.82±0.26 vs. 3.45±0.85 degrees) can be explained by the local activation of the PV sleeve under the electrodes. Overall, there was significant overlap in amplitude, maximal slope, minimal slope, and peak-angle values when comparing recordings before and after PVI. This overlap was significantly reduced (and in some completely avoided) by analyzing all parameters per type of EGM.

An automated two-step algorithm according to embodiments can facilitate clinical AF ablation procedures as it is faster, reliable, independent on operator experience, and does not requiring pacing maneuvers. Given a 100% sensitivity of the algorithm, the operator is not expected to end an ablation without complete isolation of all PVs. Given a high specificity of 87%, there is a low chance that the operator will continue ablation even though the PV is isolated (13%). As such, on top of facilitation, this algorithm may improve safety and efficacy of AF ablation (by preventing unnecessary ablation in case of isolation and prevent incomplete isolation).

A library of types and parameters as discussed hereinabove can be expanded or reconstructed to be specific for diverse catheters and systems. As such, the automated two-step algorithm can be implemented in various commercially available EAM and recording systems to guide point-by-point manual ablation. Moreover, because the algorithm does not require paired analysis and fixed position of the catheter, it could also be used in PVI guided by single shot devices (Cryoballoon, PVAC, etc.).

All electrograms in this example were recorded with a single type of circular mapping catheter. As such, the influence of catheter type, electrode size and spacing was not evaluated. This limitation can be easily overcome by constructing a new catheter-specific library.

The algorithm in this example requires the operator to specify the PV and the hemisphere for each CMC bipole. For fully automated assessment of PVI, bipole position has to be automatically detected by the navigation system.

The library of characteristics and cutoffs in this example were constructed from a dataset of patients without structural heart disease and from one center. Including more data to expand the library can be easily performed and the consequent cutoffs can be adjusted accordingly.

The invention claimed is:

1. A device for analyzing electrophysiological data, the device comprising:
   at least one electrode for generating at least one electrocardiogram recorded in a junction region between a pulmonary vein and a left atrium of the heart in a subject,
   a processing means adapted for: determining a morphology classification representative of a waveform shape for each of the at least one electrocardiogram, determining a first value representative of a likelihood that the at least one electrocardiogram comprises a pulmonary vein potential component, wherein said determining the first value takes said morphology classification into account, and
   for generating a signal indicative of a detected presence of the pulmonary vein potential component when the first value satisfies a first predetermined condition and a signal indicative of a detected absence of the pulmonary vein potential component when the first value satisfies a second predetermined condition,
   wherein the processing means is furthermore adapted for determining at least one morphological parameter indicative of at least one waveform feature for each of the at least one electrocardiogram and determining a second value representative of said likelihood that the at least one electrocardiogram comprises said pulmonary vein potential component, wherein this determining of the second value takes said at least one morphological parameter and said morphology classification into account, and
   wherein the processing means is furthermore adapted for generating a signal indicative for the detected presence of the pulmonary vein potential component when the second value satisfies a third predetermined criterion.

2. The device according to claim 1, furthermore comprising a storage means for storing previously recorded prevalence information for said morphology classification, and wherein the processing means is adapted for determining said first value taking the previously recorded prevalence information into account.

3. The device according to claim 1, wherein the processing means is furthermore adapted for preprocessing the at least one electrocardiogram by detecting, aligning and/or averaging of a plurality of atrial potentials corresponding to a plurality of heart beats in each of the at least one electrocardiogram.

4. The device according to claim 1, wherein the at least one electrode is adapted for recording a plurality of electrocardiograms from the pulmonary vein, such that each of the plurality of electrocardiograms is recorded at a plurality of different junction positions between the pulmonary vein and the left atrium of the heart of the subject.

5. The device according to claim 4, wherein the processing means is furthermore adapted for determining the morphology classification for each of the plurality of electrocardiograms.

6. The device according to claim 1, wherein the processing means is furthermore adapted for determining a number of peaks above a predetermined noise threshold and wherein the processing means is adapted for determining the morphology classification taking into account the determined number of peaks.

7. The device according to claim 1, wherein the processing means is adapted for determining an angle between an upstroke and a downstroke of a detected peak and comparing the determined angle with a predetermined angle and wherein the processing means is adapted for determining the morphology classification taking into account said comparing.

8. The device according to claim 1, wherein the processing means is adapted for selecting one of a low voltage class, a monophasic peak class, a biphasic peak class, a triphasic peak class and multiphasic peak class when determining the morphology classification.

9. The device according to claim 1, wherein the processing means is adapted for determining at least one out of a peak-to-peak amplitude, a maximum slope, a minimal slope, a sharpest peak angle and a time to coronary sinus when determining the at least one morphological parameter.

10. The device according to claim 1, wherein the processing means or the at least one electrode is adapted for determining a hemisphere classification for each of the at least one electrocardiogram.

11. The device according to claim 10, wherein the processing means is adapted for taking said hemisphere classification into account when determining the first and/or second value.

12. A method for analyzing electrophysiological data, this method comprising:
   obtaining at least one electrocardiogram recorded in a junction region between a pulmonary vein and a left atrium of the heart in a subject,
   determining a morphology classification representative of a waveform shape for each of the at least one electrocardiogram,
   determining a first value representative of a likelihood that the at least one electrocardiogram comprises a pulmonary vein potential component, wherein said determining the first value takes said morphology classification into account,
   generating a signal indicative of a detected presence of the pulmonary vein potential component when the first value satisfies a first predetermined condition and a signal indicative of a detected absence of the pulmonary vein potential component when the first value satisfies a second predetermined condition,
   determining at least one morphological parameter indicative of at least one waveform feature for each of the at least one electrocardiogram,
   determining a second value representative of said likelihood that the at least one electrocardiogram comprises said pulmonary vein potential component, wherein this determining of the second value takes said at least one morphological parameter and said morphology classification into account, and
   generating a signal indicative for the detected presence of the pulmonary vein potential component when the second value satisfies a third predetermined criterion.

13. The method according to claim 12, wherein the steps of:
   determining at least one morphological parameter,
   determining the second value and
   generating the signal indicative for the detected presence of the pulmonary vein potential component when the second value satisfies the third predetermined criterion are only performed when the first value does not satisfy the first criterion and does not satisfy the second criterion.

14. The method according to claim 12 in which determining said first value comprises taking previously recorded prevalence information for said morphology classification into account.

15. The method according to claim 12, wherein determining the morphology classification comprises determining a number of peaks above a predetermined noise threshold.

16. The method according to claim 12, wherein determining the morphology classification comprises determining an angle between an upstroke and a downstroke of a detected peak and comparing the determined angle with a predetermined threshold.

17. The method according to claim 12, wherein determining the morphology classification comprises selecting one of: a low voltage class, a monophasic peak class, a biphasic peak class, a triphasic peak class and a multiphasic peak class.

18. The method according to claim 12, furthermore comprising obtaining a hemisphere classification for the at least one electrocardiogram.

19. The method according to claim 18, wherein determining the first value and/or second value takes said hemisphere classification into account.

20. A computer program stored on a computer readable medium configured to carry out the method according to claim 12.

* * * * *